US009046481B2

United States Patent
Edler et al.

(10) Patent No.: US 9,046,481 B2
(45) Date of Patent: Jun. 2, 2015

(54) METHOD FOR THE LASER SPECTROSCOPY OF GASES

(71) Applicant: Sick AG, Waldkirch/ Breisgau (DE)

(72) Inventors: Julian Edler, Emmendingen (DE); Thomas Beyer, Freiburg (DE); Rolf Disch, Eichstetten (DE)

(73) Assignee: SICK AG, Waldkirch/Breisgau (DE)

( * ) Notice: Subject to any disclaimer, the term of this patent is extended or adjusted under 35 U.S.C. 154(b) by 0 days.

(21) Appl. No.: 14/279,369

(22) Filed: May 16, 2014

(65) Prior Publication Data
US 2014/0340684 A1    Nov. 20, 2014

(30) Foreign Application Priority Data
May 17, 2013   (EP) .................................. 13168237

(51) Int. Cl.
*G01N 21/00* (2006.01)
*G01N 21/17* (2006.01)
*G01N 21/31* (2006.01)
(Continued)

(52) U.S. Cl.
CPC ............ *G01N 21/39* (2013.01); *G01N 21/3504* (2013.01); *G01J 3/433* (2013.01); *G01N 21/274* (2013.01); *G01N 21/3554* (2013.01); *G01N 2021/399* (2013.01); *G01N 2201/0691* (2013.01); *G01N 2201/1211* (2013.01); *G01N 2201/1215* (2013.01); *G01N 2201/1218* (2013.01)

(58) Field of Classification Search
None
See application file for complete search history.

(56) References Cited

U.S. PATENT DOCUMENTS 5,929,442 A * 7/1999 Higashi .................... 250/339.13
6,519,039 B1 * 2/2003 Morishita et al. ............. 356/437
(Continued)

FOREIGN PATENT DOCUMENTS

DE    19840345 A1    3/2000
DE    10238356 A1    1/2004
(Continued)

OTHER PUBLICATIONS

European Search Report dated Nov. 4, 2013 corresponding to application No. 13168237.9-1554.
(Continued)

*Primary Examiner* — Kara E Geisel
*Assistant Examiner* — Jarreas C Underwood
(74) *Attorney, Agent, or Firm* — Nath, Goldberg & Meyer; Jerald L. Meyer; Tiffany A. Johnson

(57) ABSTRACT

A method of determining a concentration of a gas in a sample and/or the composition of a gas using a spectrometer comprises transmitting of radiation whose wavelength substantially continuously runs through a wavelength range, wherein the continuous running through of the wavelength range is overlaid by a wavelength modulation; measuring of an absorption signal as a function of the wavelength of the radiation; converting of the absorption signal into first and second derivative signals; deriving of a first and a second measured gas concentration value from the first and the second derivative signals, respectively; and determining of the concentration and/or the composition of the gas from at least the first measured gas concentration value, wherein the wavelength modulation is adapted in response to a change of a state variable of the gas such that a ratio between the first and the second measured gas concentration values is kept substantially constant.

17 Claims, 1 Drawing Sheet

Figure 1:
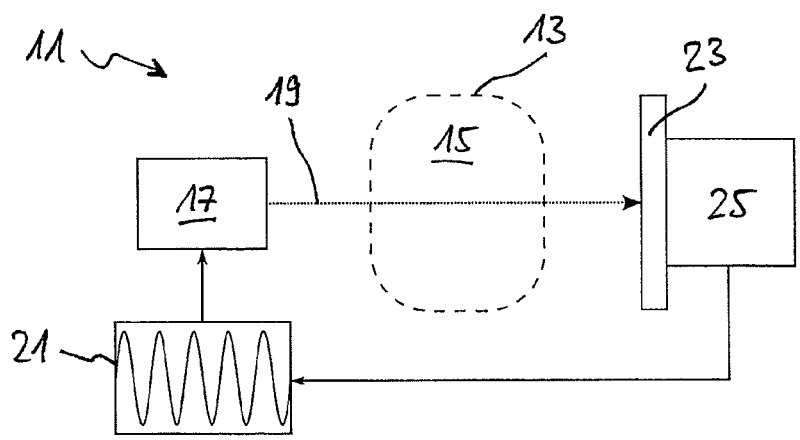

(51) Int. Cl.
*G01N 21/39* (2006.01)
*G01N 21/3504* (2014.01)
*G01J 3/433* (2006.01)
*G01N 21/27* (2006.01)
*G01N 21/3554* (2014.01)

(56) References Cited

U.S. PATENT DOCUMENTS

| | | | |
|---|---|---|---|
| 6,636,316 B1 * | 10/2003 | Matsumoto et al. | 356/437 |
| 7,969,576 B1 | 6/2011 | Buckley et al. | |
| 8,073,637 B2 * | 12/2011 | Cline et al. | 702/28 |
| 2007/0295908 A1 | 12/2007 | Wilkins et al. | |
| 2008/0225296 A1 | 9/2008 | Liu et al. | |
| 2010/0089117 A1 | 4/2010 | Liu et al. | |
| 2011/0181877 A1 | 7/2011 | Liu et al. | |
| 2014/0067282 A1 | 3/2014 | Beyer et al. | |

FOREIGN PATENT DOCUMENTS

| | | |
|---|---|---|
| EP | 1873513 A2 | 1/2008 |
| EP | 2520925 A1 | 11/2012 |
| WO | 2008112955 A1 | 9/2008 |

OTHER PUBLICATIONS

Jian Bao, et al: "Temperature Dependent of High Sensitive Diode Laser Harmonic Detection for CO Molecule", Proceedings of SPIE, May 12, 2005, pp. 747-754.

"Frequency-modulation spectrotroscopy for trace species detection: theory and comparison among experimental methods", Joel A. Silver, Feb. 20, 1992, vol. 31, No. 6, Applied Optics.

* cited by examiner

METHOD FOR THE LASER SPECTROSCOPY OF GASES

The invention relates to a method of determining a concentration of gases in a sample and/or the composition of a gas using a spectrometer. The method comprises the transmission of radiation, the measurement of an absorption signal, the conversion of the absorption signal into a derivative signal, the derivation of a measured gas concentration value from the derivative signal as well as the determination of the concentration and/or the composition of the gas from the measured gas concentration value, wherein a wavelength modulation of the radiation is adapted in response to a change of a state variable of the gas. The invention also relates to a spectrometer for the carrying out of such a method.

It is known for the examination of a gas sample as to its composition and in particular as to the concentration of a specific gas of the sample to derive this information using spectroscopy with reference to the specific absorption of radiation such as light through different gases or gas mixtures. Laser spectrometers are typically used for this purpose in which the light of a laser is irradiated through the sample which is, for example, located in a measurement space, for instance a measurement cell, or is conducted through a measurement space. With a known extent of the sample in the direction of laser propagation (extent of the measurement space), the absorption coefficient depending on the wavelength of the irradiated laser light can be determined in accordance with Lambert-Beer's law. A conclusion can be drawn on the concentration of a gas or its portion in the sample from the comparison of an absorption spectrum obtained in this manner using spectra known for different gases.

Different gases have different typical wavelengths at which they have especially high absorption. The corresponding maxima in the absorption spectrum which correspond to minima in the transmission spectrum are ideally sharp absorption lines. Due the blur relationship, to the pressure of the gas and to the temperature dependent Doppler effect, real absorption lines are, however, widened to form a specific absorption line shape. As a rule, it substantially has a Voigt profile which results on the folding of a Gaussian curve which is typical for a temperature dependent Doppler broadening with a Lorentz curve whose width is typically pressure dependent.

A whole wavelength range is therefore examined for the measurement of one or more such absorption lines in an absorption spectrum in that the laser of the spectrometer, for example, runs through a linear wavelength ramp. In this respect, the linear ramp can also be part of a saw tooth function or of a triangle function to run through the same wavelength range a plurality of times. The wavelength range is selected such that one or more absorption lines of the gas to be examined are covered by it. Provision can also be made to run through a plurality of disjunctive wavelength ranges in order to detect different absorption lines of the same gas and/or of different gases of the sample.

An extension of this direct spectroscopy is represented by wavelength modulation spectroscopy in which the substantially continuous running through of the wavelength range is overlaid by a modulation of the wavelength which is fast with respect to it. This wavelength modulation is typically sinusoidal with a fixedly predefined modulation frequency. The wavelength modulation can, however, differ from a harmonic extent since a real laser as a rule does not perfectly convert the modulation, predefined, for example, as a modulated current signal or voltage signal, into a modulation of the wavelength. Since the absorption spectrum acts as a transfer function, the wavelength modulation of the laser light is converted by the sample due to the absorption into a correspondingly modulated absorption signal which is recorded by the spectrometer.

The portions at the modulation frequency and at whole-number multiples of the modulation frequency are determined from the modulated absorption signal for the evaluation. This can take place, for example using phase-sensitive amplifiers, typically lock-in amplifiers, or by cacluation processing, for instance by means of a Fourier analysis. The signals thus determined, which indicate the portion of the modulated absorption signal at the modulation frequency or at a multiple of the modulation frequency for every wavelength, are also called derivative signals since they substantially, i.e. in particular for the borderline case of small modulation amplitudes, correspond to the (mathematical) derivations of the absorption spectrum. The portion at the modulation frequency itself in this respect corresponds to the first derivation and is also called a 1f signal; the portion at double the modulation frequency is called a 2f signal and corresponds to the second derivation, etc.

On the basis of this relationship, the derivative signals substantially contain the same information which is also contained in the direct absorption signal so that the gas concentration or the sample composition can also be determined from a respective derivative signal. The advantage of the use of the derivative signals is in this respect that the information to be determined can be displaced into higher frequency ranges in which the signal to noise ratio is as a rule better than in low frequency ranges. In addition, background signals which falsify the absorption spectrum as base lines to be deducted can be partly eliminated by the derivative signals. For example, the influence of a constant offset is eliminated in the 1f signal; in the 2f signal the influence of any desired linear base lines, etc. The higher the degree of the derivative signal, the more complex base lines are filtered from the signal, but the lower the signal intensity becomes. For this reason, the 2f signal is typically used as a good compromise between the advantages and disadvantages of higher derivations for the evaluation. A measured gas concentration value can then be derived from the derivative signal which is a measure for the concentration and/or the composition of the gas.

A method for gas analysis using laser spectroscopy according to the principle of wavelength modulation spectroscopy is described in EP 1 873 513 A2. It is in particular represented therein how, as part of the signal evaluation, conclusions can be drawn on parameters such as the concentration of a gas from the 2f signal of an absorption spectrum. It is furthermore described that, on the determination of the gas concentration, variable conditions, for example changes of state variables of the gas such as pressure, temperature and external gas influences, can be taken into account which are determined as part of a calibration.

Such a calibration can be very complex since the respective falsifying influence of as many combinations of the variable parameters as possible on the measured gas concentration value has to be determined for as many such combinations which can be considered as possible. In addition, the extent of the falsification, in particular for parameters which relates to device properties, can vary over time so that the calibration has to be repeated at regular intervals to adapt to the changed influences.

The measured gas concentration value can, however, not only depend on the gas concentration itself and on the named falsifying influences, but in particular also on the selected wavelength modulation. It is therefore known to adapt the amplitude of the wavelength modulation such that falsifying influences, in particular of the pressure of the gas, on the measured gas concentration value are already compensated on the measurement and not only as part of a downstream evaluation.

For a specific pressure range as part of a calibration, EP 2 520 925 A1, for example, proposes determining and subsequently using in the measurement that amplitude of the wavelength modulation at which the influence of the pressure on the measured gas concentration value is so small that it can essentially be neglected. In WO 2008/112955 A1, a spectrometer for wavelength modulation spectroscopy is described which comprises a pressure sensor for measuring the current pressure of the gas and in which the amplitude of the wavelength modulation is adapted in dependence on the measured pressure. The amplitude is in this respect changed just such that the influence of the pressure on the measured gas concentration value is compensated. These methods are, however, comparatively complex to the extent that a separate calibration process has to be carried out for determining the modulation amplitude or the spectrometer has to comprise a pressure sensor for determining the pressure of the sample.

It is therefore an object of the invention to provide a method of determining a concentration of a gas in a sample and/or the composition of a gas in a sample using a spectrometer in which the falsifying influence of a state variable of the gas to be measured can already be compensated in the measurement in a simple and inexpensive manner, in particular independently of a separate pressure sensor, of external gas influences and of the concentration of the gas to be measured.

This object is satisfied by a method including the conversion of the absorption signal into a second derivative signal as well as the derivation of at least one second measured gas concentration value from the second derivative signal and in that the wavelength modulation is adapted, preferably continuously, such that a ratio between the first measured gas concentration value and the second measured gas concentration value is kept substantially constant. The object is correspondingly satisfied by a spectrometer which is adapted to carry out the method in accordance with the invention. Preferred further developments are the subject of dependent claims.

Values are to be understood as measured gas concentration values in this respect which can be derived from respective derivative signals, for example in that they indicate an area or a similar measure which can be determined at the derivative signals and which contain information on the gas concentration to be measured and/or on the composition of the gas to be measured as measured values. The measured gas concentration values are measured values which reflect the concentration of the gas. The determination of the gas concentration can in this respect mean the determination of the gas concentration in a sample, which term should also include the determination of the concentration of a gas component in a gas or the determination of the composition of a gas.

The first measured gas concentration value and the second measured gas concentration value can be derived in the same manner or in a different manner from the first or second derivative signals respectively. For example, the first and the second measured gas concentration values can be a level, a spacing, a width or an area of the respective derivative signal or the first measured gas concentration value can e.g. be a level of the first derivative signal and the second measured gas concentration value can e.g. be an area of the second derivative signal.

The expression "first derivative signal" is in this respect not restricted to the derivative signal which corresponds to the first derivation of the absorption signal (1f signal), but can designate any one of the derivative signals (1f, 2f, etc.). The same applies to the expression "second derivative signal" which is not to be understood as limited to the 2f signal. The second derivative signal is, however, preferably a different signal than the first derivative signal.

In the method in accordance with the invention, it is therefore not the state variable of the gas which has a falsifying effect on the measured gas concentration value which is directly monitored to adapt the wavelength modulation to a change in the state variable. The adaptation of the wavelength modulation rather takes place with respect to changes in the absorption signal which have an effect on the first and the second derivative signals and, derived from this, on the first and second measured gas concentration values. For this reason, the state variable does not have to be detected by means of a separate sensor.

Finally, the adaptation of the wavelength modulation also takes place in response to a change of the state variable in the method in accordance with the invention. However, this change is determined with reference to the anyway measured absorption signal—namely via the ratio of two measured gas concentration values which are derived from derivative signals of the absorption signal—and not by a separate measurement of the state variable. The named ratio in this respect replaces the state variable as the regulation value for the adaptation.

The adaptation of the wavelength modulation can in particular take place continuously, that is in the sense of a continuous regulation. Accordingly, the respectively present actual value of the ratio between the first and the second measured gas concentration values is continuously compared with a ratio predefined as the desired value. On a deviation of the actual value from the desired value, the wavelength modulation is adapted according to known regulation principles such that the correction counters the deviation in order to compensate the deviation as largely as possible. In this manner, the actual ratio is kept substantially constant at the predefined desired value. The desired value can in this respect be predefined externally or can, however, be determined within the method itself, for example by looking up in a table and/or in dependence on a state variable of the gas or on other parameters of the measurement.

It is in particular utilized in the method in accordance with the invention that a change in the state variable of the gas can have a different effect on two different derivative signals of the same absorption signal. The influence of the state variable on the measurement can therefore be derived by a combined observation of the information from two different derivative signals (the first derivative signal and the second derivative signal). This combined observation actually takes place by the forming of the ratio. If a measured gas concentration value were used directly as the regulation value to be kept constant, information on the gas concentration could no longer be obtained from it since this information would also be "regulated away". Since, however, a ratio of two measured gas concentration values is kept constant, the influence of the state variable can specifically be "regulated away", while the information on the gas concentration is maintained and can be obtained from the first, the second or another measured gas concentration value.

The adaptation of the wavelength modulation can comprise different adaptations and take place in different manners. The adaptation of the wavelength modulation is in particular an adaptation of its amplitude. Alternatively or additionally, the frequency of the wavelength modulation can also be adapted.

The wavelength modulation can be continuously optimized by the method in accordance with the invention despite absorption line shapes variable in dependence on state variables of the gas. This optimization of the wavelength modulation has the additional advantage that a calibration of the measurement to the actual properties of the radiation source, e.g. of the laser, can be omitted since changes of these properties can largely be compensated within the framework of the method in accordance with the invention. The radiation source can namely admittedly have differences from default values with respect to the actually transmitted radiation. These differences can, however, largely be compensated within the framework of the method in accordance with the invention.

In accordance with an advantageous embodiment, the first and/or the second derivative signals is/are normed in dependence on an intensity of the radiation or of an intensity of the absorption signal. In this respect, the norming can in particular take place proportionally to the intensity. The intensity can, for example, be measured as a portion of the absorption signal or separately therefrom as the intensity of the radiation received, for instance, by means of the detector of a spectrometer.

The at least one state variable of the gas to whose change the wavelength modulation is adapted preferably comprises a pressure and/or an external influence of the gas. For example, the ratio to be kept constant can be selected such that the dependence of the measurement on the pressure of the gas and/or on an external gas influence of the gas is compensated. If the state variable comprises at least the pressure of the gas, a pressure sensor for determining the pressure of the gas for a subsequent pressure correction of the measured data can advantageously be dispensed with. If the state variable comprises at least one external gas influence of the gas, the broadening of the absorption signal due to any unknown external gas portions in the examined sample also does not need to be taken into account separately in the evaluation of the measurement.

In an advantageous further development, the at least one first measured gas concentration value and/or the at least one second measured gas concentration value is/are derived from a level of an extreme, from a spacing between a maximum and a minimum, from a width or from an area of the derivative signal. The level of an extreme can, for example, be the level of a central maximum in an absorption wavelength of the gas. If the respective derivative signal is a derivative signal which corresponds to an even-number derivation of the absorption signal (2f, 4f, etc.), this signal as a rule has a dominating maximum at the central wavelength of the respective absorption line of the gas and has a respective minimum symmetrically at both sides of this maximum. The value-based spacing of the central maximum from one of the two minima or from an average value of the two minima can be used as the named spacing. Derivative signals which correspond to odd-number derivations of the absorption signal (1f, 3f, etc.) are as a rule point-symmetrical to the central wavelength of the respective absorption line and have a zero crossing at the central wavelength, a maximum adjacent thereto on the one side as well as a minimum adjacent thereto on the other side of the zero crossing. In this case, the value-based spacing of this maximum and of this minimum can be used for the determination of the named area. The named width is preferably a full width at half maximum of an extreme of the respective derivative signal or a spacing between two extremes, between two zero crossings or between one extreme and one zero crossing of this derivative signal. Substantially all pronounced and clearly identifiable points of the derivative signal can therefore be used for determining the width which make it possible to determine the degree by which the absorption line is broadened by different possible influences. An area of the respective derivative signal is, for example, an area enclosed between the x axis and the derivative signal, with the area being able to be restricted, for example, to a wavelength range between two zero crossings and with area portions beneath the x axis being able to be deducted from area portions above the x axis or to be added to them.

It is furthermore advantageous if the ratio to be kept substantially constant is fixed in dependence on a pressure range of the gas. For example, the ratio pressures to be kept constant for comparatively high can be fixed to a first value and for comparatively low pressures to a second value from which a selection can be made. Finer gradations up to a continuous connection between the ratio and the pressure range are, however, also possible. The pressure range can in this respect be predefined from external or estimated. In this respect, it is not a question of measuring the exact pressure, but rather of only determining a range in which the actual pressure lies with at least some probability. Even if in general different ratios could be used as a regulating value independently of a respective pressure range, some ratios may be more suitable than others to compensate the influence of the state variable in this pressure range in dependence on the pressure range.

The ratio to be kept substantially constant is preferably fixed such that the first measured gas concentration value entering into this ratio is substantially at a maximum. In general, the aim of compensating the influence of the at least one state variable on the measurement in the measurement data by adapting the wavelength modulation can be achieved using different ratios than the respective desired value of a regulation. It is, however, advantageous to keep such a ratio constant at which at least one (the first) of the measured gas concentration values is particularly large, in particular in the pressure range to be expected. In this manner, at least this measured gas concentration value has a particularly good signal to noise ratio, whereas the signal to noise ratio of the other measured gas concentration value can be worse. Since a simultaneous optimization of the signal to noise ratio of the first and second measured gas concentration values is not generally possible, the ratio to be kept constant is selected in accordance with this further development such that at least one measured gas concentration value becomes maximum and therefore has an optimized signal to noise ratio. This low-noise measured gas concentration value can then advantageously be used for determining the concentration and/or the composition of the gas, whereas in contrast to this the other measured gas concentration value entering into the ratio does not have an optimized signal to noise ratio and is therefore preferably not used for the concentration determination. The regulation to a constant ratio is substantially not thereby negatively influenced that a measured gas concentration value is directly noise-optimized, whereas it is accepted that the other measured gas concentration value has a worse signal to noise ratio.

In accordance with a further development, the concentration and/or the composition of the gas is/are determined from the first measured gas concentration value while taking account of at least one calibration function which is determined in dependence on the ratio be to be kept substantially constant. A calibration function can in particular be provided also to compensate such falsifying influences on the measurement which are not compensated by the adaptation of the wavelength modulation which is additionally applied on the determination of the concentration and/or the composition of the gas from the first measured gas concentration value. In a conventional process, this calibration function would represent the only compensation of falsifying influences on the measurement. The calibration function would in particular also take account of the influences of at least that one state variable whose influence is eliminated in the first measured gas concentration value due to the method in accordance with the invention. On a use of the method in accordance with the invention, the calibration function therefore advantageously only has to compensate a smaller number of falsifying influences and can therefore be substantially less complex than a conventional calibration function. The calibration function can, for example, be a function of the state variables of the gas to be taken into account.

The more state variables which have to be taken into account, the more dimensions the calibration function has. The dimensionality of the calibration function can, however, be reduced by the method in accordance with the invention. For example, instead of a calibration function which takes account of the pressure, an external gas influence and the temperature of the gas, a calibration function can be provided in which only the temperature has to be taken into account. Whereas for the determination of a calibration function, which takes account of the pressure, the external gas influence and the temperature complex, test measurements have to be carried out at different pressures, external gas influences and temperatures, a calibration function which only takes the temperature into account can also be determined by calculation since the temperature relationship is a purely physical, known relationship. The further calibration of the measured data is thus also simplified by the method in accordance with the invention. Instead of an area or of a hyperarea in a multi-dimensional space, the calibration function can e.g. be a simple calibration curve, in particular dependent only on one parameter or on a few parameters.

Since the calibration function is moreover fixed in dependence on the ratio to be kept substantially constant, the calibration function is particularly well suited to compensate just those falsifying portions of the measurement signal which are not compensated by the ratio kept constant. Corresponding calibration functions can in particular already be determined for different ratios prior to a respective measurement. Depending on which ratio is selected for the measurement (e.g. in dependence on a pressure range), a suitable calibration function can then simply be looked up and taken into account for the determination of the concentration and/or the composition of the gas.

In a further development, the concentration and/or composition of the gas is/are determined from the first measured gas concentration value while taking account of at least one calibration function, with only such calibration functions being taken into account by which external gas influences and/or influences of the pressure on the absorption signal cannot be compensated. Such calibration functions are in particular taken into account by which at least influences of the temperature and/or of device properties on the absorption signal can substantially be compensated. External gas influences and/or influences of the pressure of the gas can already be compensated in the measurement via the adaptation of the wavelength modulation by the method in accordance with the invention. The calibration function can thus advantageously be restricted to the taking into account of other influences such as the influences of the temperature and/or of device properties. In this respect, the influence of the temperature on the absorption signal is a known, purely physical relationship which can be taken into account in a simple manner by means of a calibration function.

It is furthermore advantageous if the concentration and/or the composition of the gas is/are determined from at least one first measured gas concentration value derived from the first derivative signal without taking account of a measured gas concentration value derived from the second derivative signal. Ideally, the concentration of the gas is determined from at least one measured gas concentration value with a signal to noise ratio which is at a maximum where possible. Since in accordance with the invention the ratio between the first measured gas concentration value and the second measured gas concentration value is kept substantially constant, the signal to noise ratio of both the first measured gas concentration value and the second measured gas concentration value can, however, not be simultaneously maximized. It is therefore advantageous if the determination of the concentration and/or of the composition of the gas is based only on one of the derivative signals, namely preferably that one with the better signal to noise ratio. The first measured gas concentration value as a rule in particular has the better signal to noise ratio in conjunction with an embodiment in which the ratio is fixed such that the first measured gas concentration value is substantially at a maximum so that preferably only this measured gas concentration value is used for determining the concentration and/or the composition of the gas.

It is furthermore advantageous if the concentration and/or the composition of the gas is/are determined in dependence on the pressure from a first measured gas concentration value or from a second measured gas concentration value. In other words, it is not always only a single measured gas concentration value which has to be used for determining the concentration and/or the composition of the gas, but also two first measured gas concentration values can be used. The decision as to whether one or two first measured gas concentration values are used depends on the pressure or on a pressure range (estimated or determined in another manner) of the gas. Since the two first measured gas concentration values are "first" measured gas concentration values, they are both derived from the same (first) derivative signal. For example, one of the two first measured gas concentration signals can be a signal level and the other can be a signal width of the first derivative signal.

The taking into account of two first measured gas concentration values is in particular useful and necessary for a correct determination of the concentration and/or of the composition of the gas when the absorption signal differs from an ideal Lorentz curve and is broadened, that is has substantial portions of a Gaussian curve. At high pressures, the portion of the Lorentz curve dominates the absorption line shape. At lower pressures, the portion of the Gaussian curve increases so that it is possible that a single measured gas concentration value is no longer sufficient for the determination of the concentration and/or the composition of the gas. It is therefore particularly preferred if the concentration and/or the composition of the gas at a pressure in a high pressure range is/are determined from a first measured gas concentration value and at a pressure in a low pressure range from two first measured gas concentration values.

The invention also relates to a spectrometer which is adapted for carrying out the method in accordance with the invention, in particular in accordance with one of the shown embodiments. Such a spectrometer can, for example, carry out the respective method very largely in an automated fashion or in a partly automated fashion, with in the last-named case a user being able to be guided through individual steps of the method, for instance by means of a display device of the spectrometer. The spectrometer can furthermore comprise a processing unit, for example a microprocessor, on which the method in accordance with the invention or parts thereof are stored and can be executed as routines.

It is further preferred if the spectrometer comprises one or more radiation sources, in particular in the form of respective lasers, preferably diode lasers, for transmitting the radiation. The use of a laser makes it possible to obtain radiation of high intensity with a sharply defined wavelength in a simple manner. The wavelength of this laser is preferably moreover adjustable. In particular diode lasers are suitable for this purpose, for instance in the manner of a vertical cavity diode laser or of a distributed feedback diode laser which are preferably used in a spectrometer in accordance with the invention. Other radiation sources are, however, also conceivable, for instance quantum cascade lasers, interband cascade lasers, solid state lasers or gas lasers. The use of a plurality of radiation sources can serve, for example, to be able to cover a larger wavelength range.

It is furthermore advantageous for carrying out the method in accordance with the invention if the wavelength of a respective light source of the spectrometer can be precisely set and can ideally be varied continuously over a large wavelength range for the wavelength-dependent measurement of the absorption signal. To obtain radiation of a sharp wavelength, filters or grids can, for example, be inserted before a conventional radiation source.

The spectrometer preferably comprises a detector for measuring the absorption signal, the detector being able to be, for example, a silicon detector, an indium gallium arsenide detector, a mercury cadmium telluride detector, a germanium detector or an indium arsenide detector.

In particular White cells and Herriott cells can be considered as measurement cells of the detector by which in particular the optical path length is defined within which the radiation is absorbed by the gas.

In a preferred embodiment, the spectrometer comprises a phase-sensitive amplifier or a processing unit at least suitable for the Fourier transformation of the absorption signal for converting the absorption signal. The processing unit can in particular be a processing unit which is also used for controlling the spectrometer. The phase sensitive amplifier is preferably a lock-in amplifier which can be configured as analog or digital. Respective derivative signals for an absorption signal can be generated in a simple manner by means of such an amplifier or such a processing unit suitable for Fourier transformation.

The invention will be explained in the following with respect to the enclosed schematic Figures.

Figure 2:
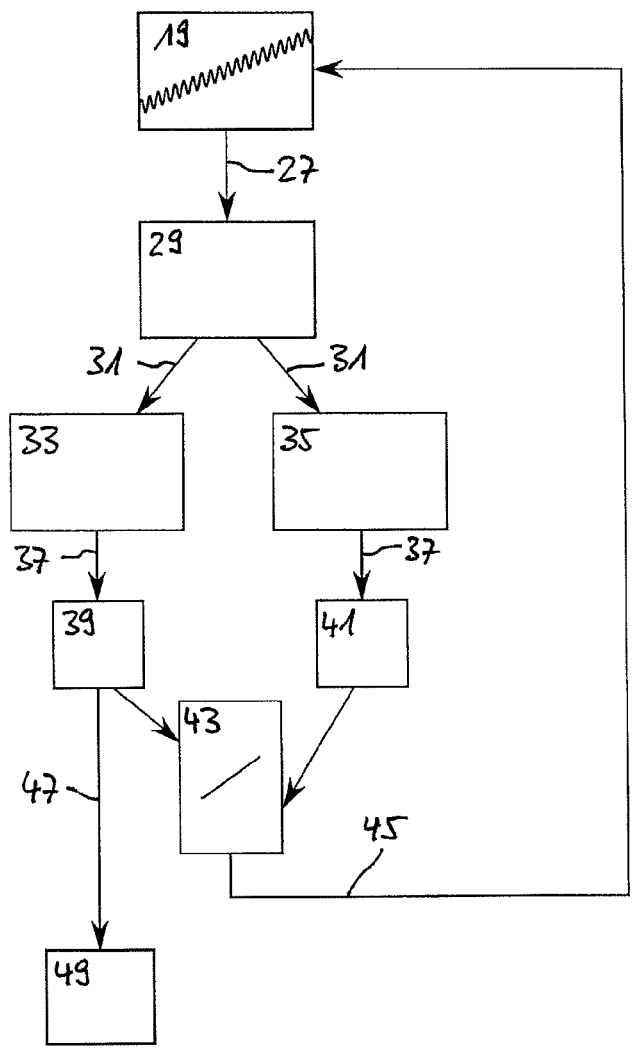

FIG. 1 shows in a schematic representation an embodiment of a spectrometer which is adapted for carrying out a method in accordance with the invention; and FIG. 2 shows in a flowchart the routine of an embodiment of the method in accordance with the invention.

The spectrometer 11 shown schematically in FIG. 1 has a measurement space in the form of a measurement cell 13 (dashed line) in which a sample of a gas 15 to be examined is contained or through which a sample of the gas 15 can flow. A radiation (19) (dotted line) can is generated and transmitted by means of a laser 17 as the radiation source of the spectrometer 11. The radiation 19 transmitted by the laser 17 is substantially monochromatic. The wavelength of the radiation 19 can, however, be uniformly adjusted over a specific wavelength range.

The continuous running through of the wavelength range is overlaid by a wavelength modulation. In the embodiment shown, a modular 21 is provided for this purpose in the form of a function generator which outputs a substantially harmonic modulation to the laser 17. In accordance with the signal the laser 17 receives from the modulator 21, the laser 17 modulates the radiation 19 it transmits. Alternatively, the modulator 21 can itself already overlay a continuous running through of a region with a substantially harmonic modulation so that the laser 17 can directly use the signal of the modulator 21 as a control signal for the wavelength of the transmitted radiation 19. The modulator 21 can in particular be integrated in the laser 17.

The radiation 19 runs through the measurement cell 13 and is so doing is absorbed by the gas in dependence on the wavelength. Subsequently, the radiation 19 is incident onto a detector 23 of the spectrometer 11 which detects the intensity of the radiation 19 in dependence on the time. Since it is known for each point in time which wavelength the laser 17 has transmitted at this point in time, the measured intensity of the radiation 19 can be brought into relationship with the respective wavelength of the transmitted radiation 19 using this connection. Finally, in this manner, an absorption signal 29 (not shown in FIG. 1) from the absorption of the radiation 19 by the gas 15 is measured as a function of the wavelength of the radiation 19 and said absorption signal is subsequently evaluated in a processing unit 25 of the spectrometer 11 (cf. FIG. 2). The processing unit 25 is connected to the modulator 21 in order to be able to adapt the wavelength modulation of the radiation 19 in dependence on values derived from the measured absorption signal 29. In this manner, a closed regulation circuit is produced which preferably has a large time constant.

The routine of an embodiment of the method is shown in FIG. 2 as a flowchart which will be described in the following starting from the transmitted radiation 19. The wavelength of the radiation 19 substantially continuously runs through a wavelength region, with it being overlaid by a substantially harmonic wavelength modulation. The step of the measurement 27 converts the transmitted radiation 19 after it has passed through the measurement cell 13 with the gas 15 into an absorption signal 29 which describes the intensity of the radiation 19. The absorption of the radiation 19 by the gas 15 in this respect acts as a transfer function which transfers the transmitted radiation 19 into the absorption signal 29 of the radiation 19 incident on the detector 23. Corresponding to the wavelength modulation of the radiation 19, the absorption signal 29 therefore also has a time modulation.

The portions of the absorption signal 29 are determined at different multiples of the modulation frequency by means of a Fourier analysis which can be carried out in the processing unit 25. In this manner, the absorption signal 29 is converted into a first derivative signal 33 and into a second derivative signal 35 in the steps 31. In this respect, in the embodiment shown, the first derivative signal 33 corresponds to the 2f signal and the second derivative signal 35 corresponds to the 3f signal of the absorption signal 29. In a subsequent step 37, a first measured gas concentration value 39 and a second measured gas concentration value 41 respectively are derived from the first derivative signal 33 and the second derivative signal 35. These measured gas concentration values 39, 41 are e.g. respectively a spacing between a maximum and, adjacent thereto, a minimum of the first or second derivative signal in the region of an absorption line of the measured gas 15.

Subsequently, the ratio 43 between the first measured gas concentration value 39 and the second measured gas concentration value 41 is determined. This can take place, for example, by a simple quotient formation, with the individual measured gas concentration values 39, 41 being able to be previously weighted or corrected in another manner. The adaptation 45 of the wavelength modulation of the radiation 19 then takes place with the aim of keeping this ratio 43 constant or, provided it has a deviation from the desired value to be kept constant, to bring it back to the desired value. The regulation device provided for this purpose is not shown in the Figures and can, for example, be integrated in the processing unit 25. The desired value to be kept constant can in particular be selected in dependence on a pressure range in which the measurement 27 takes place.

The concentration and/or the composition 49 of the gas 15 can be determined as a final step 47 of the method from the first measured gas concentration value 39. The flowchart shown in this respect corresponds to a measurement in a rather high pressure range in which a single first measured gas concentration value 39 is sufficient for determining 47 the concentration and/or the compensation 49 of the gas 15. On a measurement in a rather low pressure range, further first measured gas concentration values 39' (not shown) can be derived from the first derivative signal 33 in the step 37 in addition to the first measured gas concentration value 39 and to the second measured gas concentration value 41. The concentration and/or the composition 49 of the gas 15 can then also be reliably determined at low pressures from the two first measured gas concentration values 39, 39' which can e.g. be a signal level or a signal width of the derivative signal 33.

Reference Numeral List

11 spectrometer
11 measurement cell
15 gas
17 laser
19 radiation
21 modulator
23 detector
25 processing unit
27 step of measurement
29 absorption signal
31 step of conversion
33 first derivative signal
35 second derivative signal
37 step of derivation
39 first measured gas concentration value
41 second measured gas concentration value
43 ratio
45 step of adaptation
47 step of determination
49 concentration and/or the composition

What is claimed is:

1. A method of determining a concentration of a gas in a sample and/or the composition of a gas using a spectrometer comprising the steps of:
    transmitting radiation having a wavelength, with the wavelength substantially continuously running through a wavelength range, wherein the continuous running through of the wavelength range is overlaid by a wavelength modulation;
    measuring an absorption signal from the absorption of the radiation by the gas as a function of the wavelength of the radiation;
    converting the absorption signal into a first derivative signal;
    deriving at least one first measured gas concentration value from the first derivative signal;
    determining at least one of the concentration and the composition of the gas from at least the first measured gas concentration value;
    converting the absorption signal into a second derivative signal;
    deriving at least one second measured gas concentration value from the second derivative signal;
    wherein the wavelength modulation is adapted in response to a change of at least one state variable of the gas, and
    wherein the wavelength modulation is adapted such that a ratio between the first measured gas concentration value and the second measured gas concentration value is kept substantially constant.

2. The method in accordance with claim 1, wherein the wavelength modulation is a substantially harmonic wavelength modulation.

3. The method in accordance with claim 1, wherein the wavelength modulation is adapted continuously such that a ratio between the first measured gas concentration value and the second measured gas concentration value is kept substantially constant.

4. The method in accordance with claim 1, wherein at least one of the first derivative signal and the second derivative signal is normed in dependence on an intensity of one of the radiation and the absorption signal.

5. The method in accordance with claim 4, wherein the at least one of the first derivative signal and the second derivative signal is normed in proportional dependence on an intensity of one of the radiation and the absorption signal.

6. The method in accordance with claim 1, wherein the at least one state variable of the gas to whose change the wavelength modulation is adapted comprises a pressure and/or an external gas influence of the gas.

7. The method in accordance with claim 1, wherein the at least one first measured gas concentration value is derived from a member selected from the group comprising a level of an extreme of the first derivative signal, a spacing between a maximum and a minimum of the first derivative signal (33), a width of the first derivative signal and an area of the first derivative signal.

8. The method in accordance with claim 1, wherein the at least one second measured gas concentration value is derived from a member selected from the group comprising a level of an extreme of the second derivative signal, a spacing between a maximum and a minimum of the second derivative signal, a width of the second derivative signal and an area of the second derivative signal.

9. The method in accordance with claim 1, wherein the ratio to be kept substantially constant is fixed in dependence on a pressure range of the gas.

10. The method in accordance with claim 1, wherein the ratio to be kept substantially constant is fixed such that the first measured gas concentration value entering into this ratio is substantially at a maximum.

11. The method in accordance with claim 1, wherein at least one of the concentration and the composition of the gas is determined from the first measured gas concentration value while taking account of at least one calibration function which is fixed in dependence on the ratio to be kept substantially constant.

12. The method in accordance with claim 1, wherein at least one of the concentration and the composition of the gas is determined from the first measured gas concentration value while taking account of at least one calibration function, wherein only such calibration functions are taken into account by means of which influences of the temperature and/or of device properties on the absorption signal can substantially be compensated, but not external gas influences and/or influences of the pressure on the absorption signal.

13. The method in accordance with claim 1, wherein at least one of the concentration and the composition of the gas is determined from at least one first measured gas concentration value derived from the first derivative signal without taking account of a second measured gas concentration value derived from the second derivative signal.

14. The method in accordance with claim 1, wherein at least one of the concentration and the composition of the gas is determined in dependence on the pressure of the gas from a first measured gas concentration value or from two first measured gas concentration values.

15. The method in accordance with claim 14, wherein the concentration and the composition of the gas is determined in dependence on the pressure of the gas from a first gas measured gas concentration value at a pressure in a high pressure range and from two first measured gas concentration values at a pressure in a low pressure range.

16. A spectrometer which is adapted to carry out a method of determining a concentration of a gas in a sample and/or the composition of a gas, the apparatus comprising:
 a transmission means for transmitting radiation having a wavelength, with the wavelength substantially continuously running through a wavelength range, wherein the continuous running through of the wavelength range is overlaid by a wavelength modulation;
 a measurement means for measuring an absorption signal from the absorption of the radiation by the gas as a function of the wavelength of the radiation;
 a conversion means for converting the absorption signal into a first derivative signal;
 a derivation means for deriving at least one first measured gas concentration value from the first derivative signal;
 a determination means for determining the concentration and/or the composition of the gas from at least the first measured gas concentration value;
 a conversion means for converting the absorption signal into a second derivative signal;
 a derivation means for deriving at least one second measured gas concentration value from the second derivative signal;
 wherein the spectrometer is adapted to carry out the wavelength modulation in response to a change of at least one state variable of the gas, and
 wherein the spectrometer is adapted to carry out the wavelength modulation such that a ratio between the first measured gas concentration value and the second measured gas concentration value is kept substantially constant.

17. The spectrometer in accordance with claim 16, further comprising one of a phase-sensitive amplifier for converting the absorption signal and a processing unit at least suitable for the Fourier transformation of the absorption signal.

* * * * *